United States Patent [19]

Barnes et al.

[11] Patent Number: 5,892,131
[45] Date of Patent: Apr. 6, 1999

[54] PROCESS FOR THE PREPARATION OF PESTICIDAL FLUOROOLEFIN COMPOUNDS

[75] Inventors: Keith Douglas Barnes, Newtown, Pa.; Yulin Hu, Plainsboro, N.J.; David Allen Hunt, Newtown, Pa.

[73] Assignee: American Cyanamid Company, Madison, N.J.

[21] Appl. No.: 865,782

[22] Filed: May 29, 1997

[51] Int. Cl.$^6$ .................................................. C07C 43/205
[52] U.S. Cl. ........................... 568/639; 568/332; 570/129
[58] Field of Search ............................. 570/129; 568/639, 568/332

[56] References Cited

U.S. PATENT DOCUMENTS

| | | | |
|---|---|---|---|
| 4,933,461 | 6/1990 | Mills | 546/239 |
| 5,248,834 | 9/1993 | Elliott et al. | 568/637 |

FOREIGN PATENT DOCUMENTS

| | | |
|---|---|---|
| 2288803 | 1/1995 | United Kingdom . |
| WO 94/06741 | 3/1994 | WIPO . |

*Primary Examiner*—Jane Fan
*Attorney, Agent, or Firm*—Joseph M. Mazzarese

[57] ABSTRACT

A process and intermediate compounds for the preparation of fluoroolefin compounds which are useful as pesticidal agents.

16 Claims, No Drawings

PROCESS FOR THE PREPARATION OF PESTICIDAL FLUOROOLEFIN COMPOUNDS

This application claims priority from copending provisional application(s) serial number 60/019,117 filed on Jun. 3, 1996.

BACKGROUND OF THE INVENTION

Fluoroolefin compounds which are useful as pesticidal agents are described in WO 94/06741 and GB 2,288,803-A. Those references also describe processes for the preparation of fluoroolefin compounds. However, those processes are not entirely satisfactory because the fluoroolefin compounds are produced in relatively low yields. Those references also fail to teach how to make the intermediate compounds of the present invention.

SUMMARY OF THE INVENTION

The present invention provides an effective and efficient process for the preparation of a pesticidal fluoroolefin compound having the structural formula I

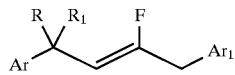

wherein
R is hydrogen or $C_1$–$C_4$alkyl, and
$R_1$ is $C_1$–$C_4$alkyl or cyclopropyl, or R and $R_1$ are taken together with the carbon atom to which they are attached to form a cyclopropyl group;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
$Ar_1$ is phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups; and
the configuration of the groups $ArCRR_1$— and —$CH_2Ar_1$ about
the double bond is predominately mutually trans,
which process comprises reacting a 4-aryl-2-fluoro-2-butene-1-ol compound having the structural formula II

wherein Ar, R and $R_1$ are as described above, with a brominating agent to form a 4-aryl-1-bromo-2-fluoro-2-butene compound having the structural formula III

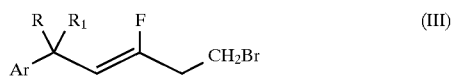

wherein Ar, R and $R_1$ are as described above, and reacting the formula III compound with a palladium catalyst, a base, and a boronic acid having the structural formula IV, a boronic anhydride having the structural formula V or a borate ester having the structural formula VI

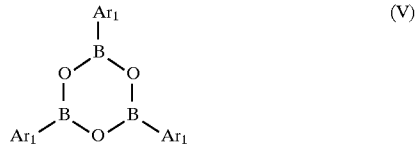

wherein $R_2$ is $C_1$–$C_4$alkyl and $Ar_1$ is as described above.

The present invention also relates to the intermediate 4-aryl-1-bromo-2-fluoro-2-butene compounds of formula III.

It is, therefore, an object of the present invention to provide an effective and efficient process for the preparation of pesticidal fluoroolefin compounds.

It is also an object of the present invention to provide intermediate compounds which are useful for the preparation of pesticidal fluoroolefin compounds.

Other objects and advantages of the present invention will be apparent to those skilled in the art from the description below and the appended claims.

DETAILED DESCRIPTION OF THE INVENTION

A preferred embodiment of the present invention comprises reacting a 4-aryl-2-fluoro-2-butene-1-ol of formula II with at least about one molar equivalent of a brominating agent, preferably in a temperature range of about 50° C. to 130° C., in the presence of a first solvent to form a 4-aryl-1-bromo-2-fluoro-2-butene of formula III, and reacting the formula III compound with about 0.001 to 0.1, preferably about 0.005 to 0.1, molar equivalent of a palladium catalyst, at least about 2 molar equivalents, preferably about 2–6 molar equivalents of a base, and a boronic acid of formula IV, preferably 1 molar equivalent of a boronic acid in a temperature range of about 50° C. to 130° C., in the presence of a second solvent.

The present invention also relates to the 4-aryl-1-bromo-2-fluoro-2-butene compounds which are utilized in the process of this invention. The 4-aryl-1-bromo-2-fluoro-2-butene compounds have the structural formula III

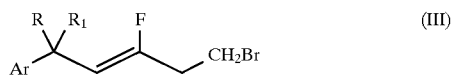

wherein
R is hydrogen or $C_1$–$C_4$alkyl, and
$R_1$ is $C_1$–$C_4$alkyl or cyclopropyl, or R and $R_1$ are taken together with the carbon atom to which they are attached to form a cyclopropyl group;
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and the configuration of the groups $ArCRR_1$— and —$CH_2Br$ about the double bond is predominately mutually trans. Exemplary of halogen hereinabove are fluorine, chlorine, bromine and iodine. The terms "$C_1$–$C_4$haloalkyl" and "$C_1$–$C_4$haloalkoxy" are defined as a $C_1$–$C_4$alkyl group and a $C_1$–$C_4$alkoxy group substituted with one or more halogen atoms, respectively.

The product formula I compounds may be isolated by diluting the reaction mixture with water and extracting the product with a suitable extraction solvent. In the isolation procedure, conventional extraction solvents such as ether, ethyl acetate, toluene, methylene chloride and the like may be utilized.

Brominating agents suitable for use in the process of this invention include, but are not limited to, bromine/triphenyl phosphine complexes, phosphorus tribromide, thionyl bromide, concentrated hydrobromic acid, and the like, and mixtures thereof. Bromine/triphenyl phosphine complexes are preferred brominating agents.

First solvents suitable for use in the present invention include, but are not limited to, aromatic hydrocarbons such as toluene, benzene, xylenes, mesitylene and the like, halogenated aromatic hydrocarbons such as chlorobenzene, fluorobenzene and the like, carboxylic acid amides such as N,N-dimethylformamide and the like, ethers such as tetrahydrofuran, dioxane and the like, and halogenated hydrocarbons such as chloroform, carbon tetrachloride and the like, and mixtures thereof. Preferred first solvents include halogenated hydrocarbons with carbon tetrachloride being more preferred.

Second solvents useful in the process of this invention include, but are not limited to, aromatic hydrocarbons such as toluene, benzene, xylenes, mesitylene and the like, halogenated aromatic hydrocarbons such as chlorobenzene, fluorobenzene and the like, carboxylic acid amides such as N,N-dimethylformamide and the like, glycols such as dimethoxyethane and the like, $C_1$–$C_4$alcohols such as methanol, ethanol and the like, ketones such as acetone and the like, and ethers such as tetrahydrofuran, dioxane and the like, and mixtures thereof, and mixtures with water. Preferred second solvents include aromatic hydrocarbons and aromatic hydrocarbon/$C_1$–$C_4$alcohol mixtures with a toluene/ethanol mixture being more preferred.

Palladium catalysts suitable for use in the present invention include, but are not limited to, palladium(0) catalysts such as bis(dibenzylideneacetone)palladium(0), tetrakis(triphenylphosphine)palladium(0) and the like, palladium (II) catalysts such as bis(acetonitrile)palladium(II) chloride, bis(triphenylphosphine)palladium(II) chloride, [1,4-bis(diphenylphosphine)-butane]palladium(II) dichloride, [1,1'-bis(diphenylphosphino)ferrocene]palladium(II) diacetate, palladium(II) acetate, palladium(II) chloride and the like, and palladium on activated carbon, and mixtures thereof. Preferred catalysts include palladium(0) catalysts with bis(dibenzylideneacetone)palladium(0) being more preferred.

Bases suitable for use in this invention include, but are not limited to, alkali metal carbonates such as sodium carbonate and potassium carbonate, alkaline earth metal carbonates such as calcium carbonate and the like, alkali metal hydrogen carbonates such as sodium hydrogen carbonate and the like, alkali metal hydroxides such as sodium hydroxide and potassium hydroxide, alkaline earth metal hydroxides such as calcium hydroxide and the like, alkali metal $C_1$–$C_6$alkoxides such as potassium tert-butoxide and the like, thallium(I) carbonate, thallium(I) $C_1$–$C_6$alkoxides, thallium(I) hydroxide, and tri($C_1$–$C_4$alkyl)amines such as trimethylamine, and mixtures thereof. Preferred bases include alkali metal carbonates with potassium carbonate being more preferred.

In another preferred embodiment of the present invention, a 4-aryl-1-bromo-2-fluoro-2-butene of formula III is reacted with a palladium catalyst, a base and a boronic acid of formula IV.

Boronic acids of formula IV, boronic anhydrides of formula V, and borate esters of formula VI may be prepared, as illustrated in Flow Diagram I, by reacting an aryl compound of formula VII with a tri($C_1$–$C_4$alkyl) borate of formula VIII to form the formula VI borate ester, and hydrolyzing the formula VI borate ester with aqueous acid to form the boronic acid of formula IV which may spontaneously combine with other formula IV compounds to form the boronic anhydride of formula V.

FLOW DIAGRAM I

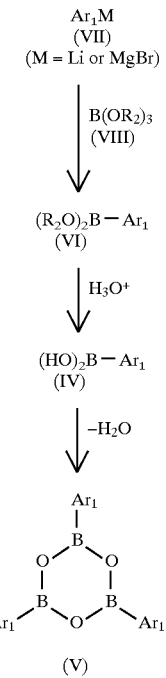

Starting 4-aryl-2-fluoro-2-butene-1-ol compounds of formula II may be prepared according to the procedures described in WO 94/06741 and GB 2,288,803-A.

In another preferred embodiment of the present invention, a 4-aryl-2-fluoro-2-butene-1-ol of formula II is reacted with a brominating agent in a temperature range of about 50° C. to 130° C., and a 4-aryl-1-bromo-2-fluoro-2-butene of formula III is reacted with a palladium catalyst, a base and a formula IV, V or VI compound in a temperature range of about 50° C. to 130° C.

Preferred formula I fluoroolefin compounds which may be prepared by the process of this invention are those wherein
  R is hydrogen and $R_1$ is isopropyl or cyclopropyl, or R and $R_1$ are methyl, or R and $R_1$ are taken together with the carbon atom to which they are attached to form a cyclopropyl group;
  Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and
  $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
    3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

The process of the present invention is also preferably used for the preparation of pesticidal fluoroolefins of formula I wherein R and $R_1$ are methyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

In order to facilitate a further understanding of the invention, the following examples are presented primarily for the purpose of illustrating more specific details thereof. The scope of the invention should not be deemed limited by the examples, but encompasses all the subject matter defined in the claims.

EXAMPLE 1

Preparation of 1-(p-Chlorophenyl)-1-(3-bromo-2-fluoropropenyl)cyclopropane, (Z)-

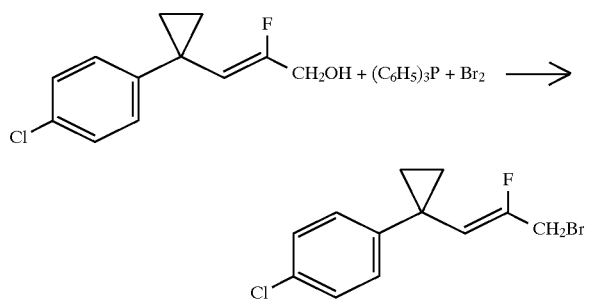

Under a nitrogen atmosphere, a solution of bromine (0.767 g, 4.8 mmol) in carbon tetrachloride at ice-water bath temperature is treated sequentially with a solution of triphenylphosphine (1.26 g, 4.8 mmol) in carbon tetrachloride and a solution of 3-[1-(p-chlorophenyl)-cyclopropyl]-2-fluoro-2-propen-1-ol, (Z)- (0.907 g, 4 mmol) in carbon tetrachloride, heated to and stirred at reflux for 70 minutes, cooled to room temperature, and poured into petroleum ether. The resultant mixture is filtered, and the filtrate is concentrated in vacuo to obtain a residue: The residue is dissolved in petroleum ether and passed through a plug of silica gel (eluted with hexanes) to obtain an oil. Flash column chromatography of the oil using silica gel and a 3:20 methylene chloride/hexanes solution gives the title product as a colorless oil (0.73 g, 63% yield) which is identified by NMR spectral analyses.

EXAMPLE 2

Preparation of 1-(p-Chlorophenyl)-1-[2-fluoro-3-(4-fluoro-3-phenoxy-3-phenoxyphenyl)propenyl]cyclopropane, (Z)-

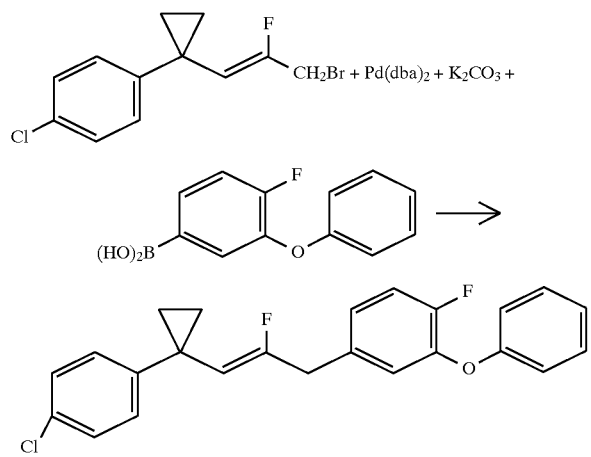

Under a nitrogen atmosphere, a mixture of 1-(p-chlorophenyl)-1-(3-bromo-2-fluoropropenyl)cyclopropane, (Z)- (0.434 g, 1.5 mmol), 4-fluoro-3-phenoxybenzeneboronic acid (0.452 g, 1.95 mmol), potassium carbonate (1.86 g, 13.5 mmol) and bis(dibenzylideneacetone) palladium(0) (Pd(dba)$_2$, 4.3 mg, 0.075 mmol) in toluene is heated at 80° C. for one hour, cooled to room temperature, diluted with water, and filtered through diatomaceous earth. The phases are separated and the aqueous phase is extracted with ethyl acetate. The organic phase and ethyl acetate extract are combined, washed with water, dried over anhydrous sodium sulfate and concentrated in vacuo to obtain a residue. Flash column chromatography of the residue using silica gel and a 3:20 methylene chloride/hexanes solution gives the title product as an oil (0.274 g, 63% yield) which is identified by NMR spectral analyses.

As can be seen from the data in Examples 1 and 2, 1-(p-chlorophenyl)-1-[2-fluoro-3-(4-fluoro-3-phenoxyphenyl)propenyl]cyclopropane, (Z)- is obtained in 40% yield from 3-[1-(p-chlorophenyl)cyclopropyl]-2-fluoro-2-propen-1-ol, (Z)-. In contrast, WO 94/06741 discloses that 1-(p-chlorophenyl)-1-[2-fluoro-3-(4-fluoro-3-phenoxyphenyl)propenyl]cyclopropane, (Z)- is obtained in 20% yield from 3-[1-(p-chlorophenyl)cyclopropyl]-2-fluoro-2-propen-1-ol, (Z)-.

EXAMPLE 3

Preparation of 1-Bromo-4-(p-chlorophenyl)-2-fluoro-4-methyl-2-pentene, (Z)-

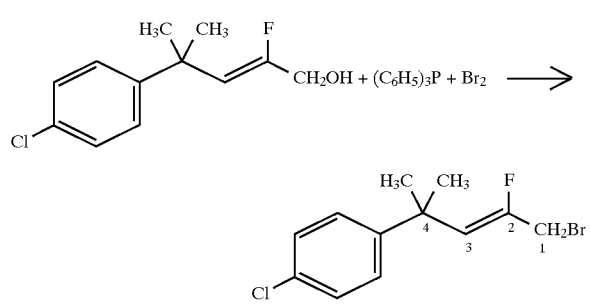

Under a nitrogen atmosphere, a solution of triphenyl phosphine (0.96 g, 4.25 mmol) in carbon tetrachloride at −5° C. is treated dropwise with a solution of bromine (0.679 g, 4.25 mmol) in carbon tetrachloride, warmed to and stirred at room temperature for 45 minutes, treated with a solution of 4-(p-chlorophenyl)-2-fluoro-4-methyl-2-penten-1-ol, (Z)- (0.81 g, 3.54 mmol) in carbon tetrachloride, refluxed for 2 hours, cooled to room temperature, and poured into petroleum ether. The resultant mixture is filtered through diatomaceous earth. The filtrate is washed sequentially with water, saturated sodium hydrogen carbonate solution and brine, dried over anhydrous sodium sulfate and concentrated in vacuo to obtain an oil. Flash column chromatography of the oil using silica gel and a 1:9 ethyl acetate/hexanes solution gives the title product as a colorless oil (0.736 g, 71% yield) which is identified by NMR spectral analyses.

EXAMPLE 4

Preparation of 4-(p-Chlorophenyl)-2-fluoro-1-(4-fluoro-3-phenoxyphenyl)-4-methyl-2-pentene, (Z)-

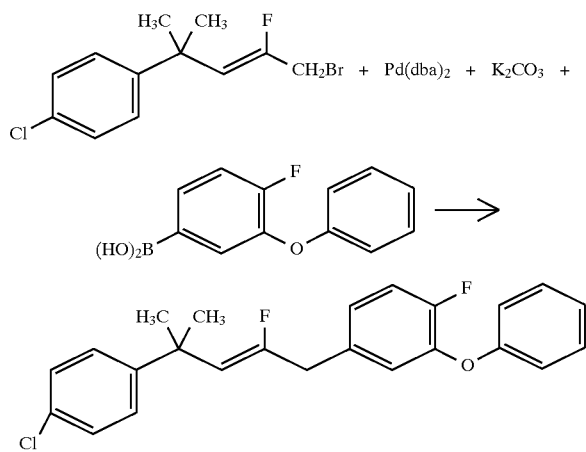

Under a nitrogen atmosphere, a mixture of 1-bromo-4-(p-chlorophenyl)-2-fluoro-4-methyl-2-pentene, (Z)- (320.8 mg, 1.1 mmol), bis(dibenzylideneacetone)palladium(0) (Pd(dba)$_2$, 31.6 mg, 0.055 mmol) in toluene (8 mL) is treated with potassium carbonate (608 mg, 4.4 mmol), degassed, treated with a solution of 4-fluoro-3-phenoxybenzeneboronic acid (331.8 mg, 1.43 mmol) in ethanol (2 mL), refluxed for 45 minutes, cooled to room temperature, and filtered through diatomaceous earth. The filtrate is diluted with ethyl acetate, and the resultant solution is washed sequentially with water and brine, dried over anhydrous sodium sulfate, and concentrated in vacuo to obtain a residue. Flash column chromatography of the residue using silica gel and a 1:9 ethyl acetate/hexanes solution gives the title product as a colorless liquid (401 mg, 91% yield) which is identified by NMR spectral analyses.

As can be seen from the data in Examples 3 and 4, 4-(p-chlorophenyl)-2-fluoro-1-(4-fluoro-3-phenoxyphenyl)-4-methyl-2-pentene, (Z)- is obtained in 65% yield from 4-(p-chlorophenyl)-2-fluoro-4-methyl-2-penten-1-ol, (Z)-. In contrast, GB 2,288,803-A discloses that 4-(p-chlorophenyl)-2-fluoro-1-(4-fluoro-3-phenoxyphenyl)-4-methyl-2-pentene, (Z)- is obtained in 37% yield from 4-(p-chlorophenyl)-2-fluoro-4-methyl-2-penten-1-ol, (Z)-.

EXAMPLE 5

Preparation of 4-Fluoro-3-phenoxybenzeneboronic acid

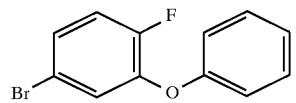

1) Mg
2) B(OCH$_3$)$_3$
3) CH$_3$CO$_2$H/H$_2$O

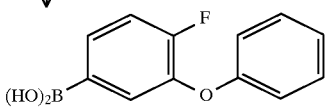

A solution of 5-bromo-2-fluorophenyl phenyl ether (8.01 g, 3 mmol) in tetrahydrofuran is added dropwise to a mixture of magnesium turnings (0.0802 g, 3.3 mmol), a crystal of iodine and a few drops of 1,2-dibromoethane in tetrahydrofuran at 50°–55° C. under nitrogen. After the addition is complete, the reaction mixture is stirred at 50°–55° C. for 70 minutes and cooled to room temperature. The cooled mixture is added over 25 minutes to a solution of trimethyl borate (4.09 mL, 3.6 mmol) in diethyl ether at dry-ice/acetone bath temperature. After the addition is complete, the mixture is stirred at dry-ice/acetone bath temperature for 20 minutes, allowed to warm to −10° C. over 25 minutes, diluted sequentially with acetic acid and water, stirred at room temperature for 30 minutes, and extracted with ether The organic extract is washed with water, dried over anhydrous sodium sulfate, and concentrated in vacuo to obtain a residue. A mixture of the residue in water is heated over a steam bath for 30 minutes, cooled to room temperature and filtered to obtain a solid which is washed with hexanes and dried to give the title product as a colorless solid (5.7 g, mp 177°–180° C., 82% yield).

We claim:

1. A process for the preparation of a fluoroolefin compound having the structural formula I

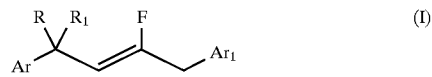

wherein

R is hydrogen or C$_1$–C$_4$alkyl, and

R$_1$ is C$_1$–C$_4$alkyl or cyclopropyl, or R and R$_1$ are taken together with the carbon atom to which they are attached to form a cyclopropyl group;

Ar is phenyl optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups, or 1- or 2-naphthyl optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups;

Ar$_1$ is phenoxyphenyl optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups, biphenyl optionally substituted with any combination of from one to five halogen, C$_1$–C$_4$alkyl, C$_1$–C$_4$haloalkyl, C$_1$–C$_4$alkoxy or C$_1$–C$_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups; and the configuration of the groups $ArCRR_1$— and —$CH_2Ar_1$ about the double bond is predominately mutually trans, which process comprises reacting a 4-aryl-2-fluoro-2-butene-1-ol compound having the structural formula II

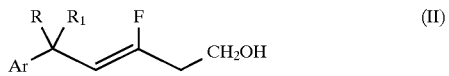

wherein Ar, R and $R_1$ are as described above with a brominating agent to form a 4-aryl-1-bromo-2-fluoro-2-butene compound having the structural formula III

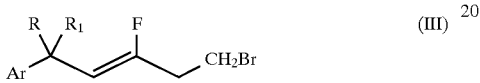

wherein Ar, R and $R_1$ are as described above, and reacting the formula III compound with a palladium catalyst, a base, and a boronic acid having the structural formula IV, a boronic anhydride having the structural formula V or a borate ester having the structural formula VI

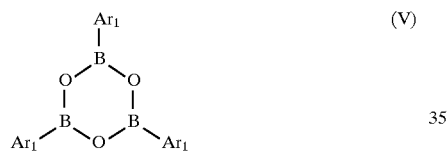

wherein $R_2$ is $C_1$–$C_4$alkyl and $Ar_1$ is as described above.

2. The process according to claim 1 wherein the brominating agent is a bromine/triphenylphosphine complex.

3. The process according to claim 1 wherein the palladium catalyst is selected from the group consisting of bis(dibenzylideneacetone)palladium(0), tetrakis(triphenylphosphine)palladium(0), bis(acetonitrile) palladium(II) chloride, bis(triphenylphosphine)palladium (II) chloride, [1,4-bis(diphenylphosphine)butane]palladium (II) dichloride, [1,1'-bis(diphenylphosphino)ferrocene] palladium(II) diacetate, palladium(II) acetate, palladium(II) chloride and palladium on activated carbon and mixtures thereof; and the base is selected from the group consisting of an alkali metal carbonate, an alkaline earth metal carbonate, an alkali metal hydrogen carbonate, an alkali metal hydroxide, an alkaline earth metal hydroxide, an alkali metal $C_1$–$C_6$alkoxide, thallium(I) carbonate, a thallium(I) $C_1$–$C_6$alkoxide, thallium(I) hydroxide and a tri($C_1$–$C_4$alkyl) amine and mixtures thereof.

4. The process according to claim 3 wherein the palladium catalyst is bis(dibenzylideneacetone)palladium(0) and the base is an alkali metal carbonate.

5. The process according to claim 1 wherein the formula III compound is reacted with a boronic acid.

6. The process according to claim 1 wherein the first reaction step is carried out in a first solvent selected from the group consisting of an aromatic hydrocarbon, a halogenated aromatic hydrocarbon, a carboxylic acid amide, an ether and a halogenated hydrocarbon and mixtures thereof; and the last reaction step is carried out in a second solvent selected from the group consisting of an aromatic hydrocarbon, a halogenated aromatic hydrocarbon, a carboxylic acid amide, a glycol, a $C_1$–$C_4$alcohol, a ketone and an ether and mixtures thereof.and mixtures with water.

7. The process according to claim 6 wherein the first solvent is a halogenated hydrocarbon and the second solvent is toluene or a toluene/ethanol mixture.

8. The process according to claim 1 wherein the formula II compound is reacted with the brominating agent at a temperature of about 50° C. to 130° C., and the formula III compound is reacted with the palladium catalyst, the base and the formula IV, V or VI compound at a temperature of about 50° C. to 130° C.

9. The process according to claim 1 wherein

R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

10. The process according to claim 9 wherein

R and $R_1$ are methyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

11. A process for the preparation of a fluoroolefin compound having the structural formula I

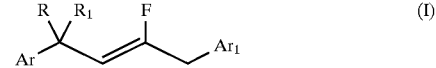

wherein

R is hydrogen or $C_1$–$C_4$alkyl, and $R_1$ is $C_1$–$C_4$alkyl or cyclopropyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

$Ar_1$ is phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups;

benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups; and the configuration of the groups $ArCRR_1$— and —$CH_2Ar_1$ about the double bond is predominately mutually trans, which process comprises reacting a 4-aryl-1-bromo-2-fluoro-2-butene compound having the structural formula III

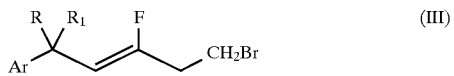
(III)

wherein Ar, R and $R_1$ are as described above with about 0.001 to 0.1 molar equivalent of a palladium catalyst, at least about 2 molar equivalents of a base, and a boronic acid having the structural formula IV, a boronic anhydride having the structural formula V or a borate ester having the structural formula VI

(IV)

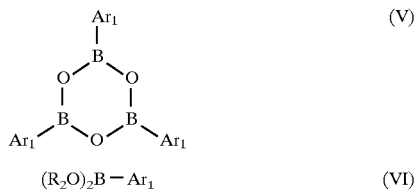
(V)

$(R_2O)_2B$—$Ar_1$ (VI)

wherein $R_2$ is $C_1$–$C_4$alkyl and $Ar_1$ is as described above, at a temperature of about 50°–130° C. in the presence of a solvent.

12. The process according to claim 11, wherein the palladium catalyst is selected from the group consisting of bis(dibenzylideneacetone)palladium(0), tetrakis(triphenylphosphine)palladium(0), bis(acetonitrile)palladium(II) chloride, bis(triphenylphosphine)palladium(II) chloride, [1,4-bis(diphenylphosphine)butane]palladium(II) dichloride, [1,1'-bis(diphenylphosphino)ferrocene]palladium(II) diacetate, palladium(II) acetate, palladium(II) chloride and palladium on activated carbon and mixtures thereof; and the base is selected from the group consisting of an alkali metal carbonate, an alkaline earth metal carbonate, an alkali metal hydrogen carbonate, an alkali metal hydroxide, an alkaline earth metal hydroxide, an alkali metal $C_1$–$C_6$alkoxide, thallium(I) carbonate, a thallium(I) $C_1$–$C_6$alkoxide, thallium(I) hydroxide and a tri($C_1$–$C_4$alkyl) amine and mixtures thereof.

13. The process according to claim 12 wherein the palladium catalyst is bis(dibenzylideneacetone)palladium(0) and the base is an alkali metal carbonate.

14. The process according to claim 11 wherein the solvent is selected from the group consisting of an aromatic hydrocarbon, a halogenated aromatic hydrocarbon, a carboxylic acid amide, a glycol, a $C_1$–$C_4$alcohol, a ketone and an ether and mixtures thereof and mixtures with water.

15. The process according to claim 11 wherein

R is hydrogen and $R_1$ is isopropyl or cyclopropyl, or R and $R_1$ are methyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

16. The process according to claim 15 wherein

R and $R_1$ are methyl, or R and $R_1$ are taken together with the carbon atom to which they are attached to form a cyclopropyl group;

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

* * * * *

UNITED STATES PATENT AND TRADEMARK OFFICE
CERTIFICATE OF CORRECTION

PATENT NO.   : 5,892,131
DATED        : April 6, 1999
INVENTOR(S)  : Keith Douglas Barnes, et al.

It is certified that error appears in the above-identified patent and that said Letters Patent is hereby corrected as shown below:

Column 1, line 62, and column 9, line 15, change the chemical structure in formula II to read:

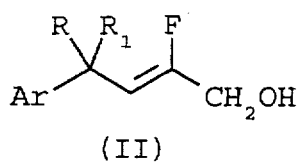

(II)

Column 2, lines 1 and 52, column 9, line 21, and column 11, line 26, change the chemical structure in formula III to read:

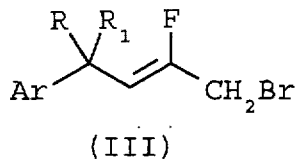

(III)

Signed and Sealed this

Twenty-seventh Day of July, 1999

Attest:

Q. TODD DICKINSON

*Attesting Officer*           *Acting Commissioner of Patents and Trademarks*